US009266718B2

(12) United States Patent
Cachemaille et al.

(10) Patent No.: US 9,266,718 B2
(45) Date of Patent: Feb. 23, 2016

(54) OUT-OF-PLANE MICRONEEDLE MANUFACTURING PROCESS

(75) Inventors: Astrid Cachemaille, Lausanne (CH); Francois Cannehan, Lausanne (CH)

(73) Assignee: DEBIOTECH S.A., Lausanne (CH)

( * ) Notice: Subject to any disclaimer, the term of this patent is extended or adjusted under 35 U.S.C. 154(b) by 789 days.

(21) Appl. No.: 13/507,368

(22) Filed: Jun. 22, 2012

(65) Prior Publication Data

US 2012/0328835 A1 Dec. 27, 2012

Related U.S. Application Data

(62) Division of application No. 12/808,334, filed as application No. PCT/IB2008/054280 on Oct. 17, 2008, now Pat. No. 8,999,177.

(30) Foreign Application Priority Data

Dec. 17, 2007 (EP) ..................................... 07123416

(51) Int. Cl.
*B81C 1/00* (2006.01)
*A61M 37/00* (2006.01)

(52) U.S. Cl.
CPC ........ *B81C 1/00111* (2013.01); *A61M 37/0015* (2013.01); *A61M 2037/0053* (2013.01); *B81B 2201/055* (2013.01); *Y10T 29/49826* (2015.01); *Y10T 428/24479* (2015.01)

(58) Field of Classification Search
CPC .................. Y10T 428/24182; A61M 37/0015; A61M 2037/0053; B81C 1/00142; B81B 2201/055
USPC .................................................. 428/120, 138
See application file for complete search history.

(56) References Cited

FOREIGN PATENT DOCUMENTS

| EP | 0 597 302 | 5/1994 |
|---|---|---|
| EP | 1 669 100 | 6/2006 |
| WO | 03/015860 | 2/2003 |
| WO | 2008/003564 | 1/2008 |

OTHER PUBLICATIONS

International Search Report for PCT/IB2008/054280, mailed May 13, 2009.
Written Opinion of the International Searching Authority for PCT/IB2008/054280, mailed May 13, 2009.
Lang W: "Silicon Microstructuring Technology", Materials Science and Engineering R: Reports, Elsevier Sequoia S.A., Lausanne, CH, vol. 17, No. 1, Sep. 1, 1996, pp. 1-55, XP004013096.

*Primary Examiner* — Alexander Thomas
(74) *Attorney, Agent, or Firm* — Nixon & Vanderhye P.C.

(57) ABSTRACT

An out-of-plane microneedle manufacturing process comprises the simultaneous creation of a network of microneedles and the creation of a polygonal shaped hat above each microneedle under formation. The process comprises the following steps: providing bridges between the hats, maintaining the bridges during the remaining microneedle manufacturing steps, removing the bridges, together with the hats, when the microneedles are formed.

6 Claims, 11 Drawing Sheets

FIGURE 2 (AA')

OUT-OF-PLANE MICRONEEDLE MANUFACTURING PROCESS

This application is a divisional application from U.S. patent application Ser. No. 12/808,334, filed Jun. 15, 2010, now U.S. Pat. No. 8,999,177, which is the U.S. national phase of International Patent Application PCT/IB2008/054280, filed Oct. 17, 2008, which designated the U.S., and which claimed priority from EP Application No. 07123416.5, filed Dec. 17, 2007, the entire contents of each of which are hereby incorporated by reference in this application.

FIELD OF INVENTION

The present invention relates to microneedles which are manufactured from a wafer, for instance a silicon wafer. The microneedles according to the invention may advantageously be used in the medical field, for intradermally administering a fluid in the body.

STATE OF THE ART

MEMS Microneedles may be classified in two groups, namely in-plane microneedles and out-of-plane microneedles. In the first group the microneedle shaft is parallel to the wafer while in the second group the shaft is perpendicular to the substrate. The out-of-plane microneedle group may itself be divided in two sub-groups, i.e. hollow microneedles and solid microneedles. The hollow microneedles have a through hole as described e.g. in patent applications WO 2002/017985 WO0217985 and WO 2003/015860. The microneedle manufacturing processes disclosed in the prior art use different designs and a combination of photolithography and etching (dry and/or wet etching) to obtain different microneedle shapes. A common feature in all those processes is the presence of a protective mask, generally made of silicon dioxide, above each microneedle under formation. This mask is commonly named "hat".

Some problems are however observed with the state-of-the-art microneedle manufacturing processes. For instance, in the manufacture of out-of-plane microneedles, the yield is limited by the difference of silicon etch rate between the centre and the border of the wafer. Because of this difference some microneedle hats (generally at the periphery of the wafer) fall before the end of the process. The consequence is that the microneedles underneath are no longer protected and as a consequence no longer etched in a controlled manner. Problems therefore arise, in particular microneedle malformation and low production yields.

GENERAL DESCRIPTION OF THE INVENTION

The problems discussed in the previous chapter are eliminated or at least notably reduced with the microneedle manufacturing process according to the invention which is characterized by the creation of bridges which link the hats between each others as well as between hats and edges during the manufacturing process.

More exactly the invention concerns an out-of-plane microneedle manufacturing process comprising the simultaneous creation of a network of microneedles and the creation of a polygonal shaped hat above each microneedle under formation, the process comprising the following steps:
  providing bridges between the hats,
  maintaining the bridges during the remaining microneedle manufacturing steps,
  removing the bridges, together with the hats, when the microneedles are formed.

In the present text, the expression "polygonal hat" has to be understood" as a closed figure consisting of straight lines joined end to end.

A "polygonal hat" in the sense of the present text also include a circle. This object May be viewed as a polygone with straight lines tending towards zero.

Like the hats, the bridges are totally removed at the end of the manufacturing process and result in no modification of the microneedle design.

The bridges are preferably made of suspended structures. They have a design which is compatible with the materials of the suspended structures and the microneedle fabrication process.

The bridges may have many different designs.

In one embodiment they are rectilinear.

In another embodiment they comprise a curved portion.

Advantageously, each bridge consists of a combination of rectilinear segments and of circle portions, e.g. of ½ and ¼ circles.

The bridge dimensions can vary depending on the distance between the microneedles as well as the distance between the microneedles and the edge of the wafer. The thickness of the bridges which is linked to the thickness of the hats can vary between 100 nm and 100 um: The width of the bridges can vary between 1 um and 100 um.

Moreover certain physical properties such as the mechanical resistance are affected by the size and shape of the bridges.

The material used must have the appropriate characteristics to support the manufacturing process. For example, for a process requiring an excellent conductivity, metal would be chosen. Multilayered bridges, in particular with three layers, offer an interesting compromise when different properties are required as for example good conductivity, high selectivity and mechanical resistance to deformation. For example, the bridges are made of three layers, namely one conductive layer between two non conductive layers.

DETAILED DESCRIPTION OF THE INVENTION

The invention is discussed below in a more detailed way with examples illustrated by the following figures.

NUMERICAL REFERENCES USED IN THE FIGURES

Figure 1:
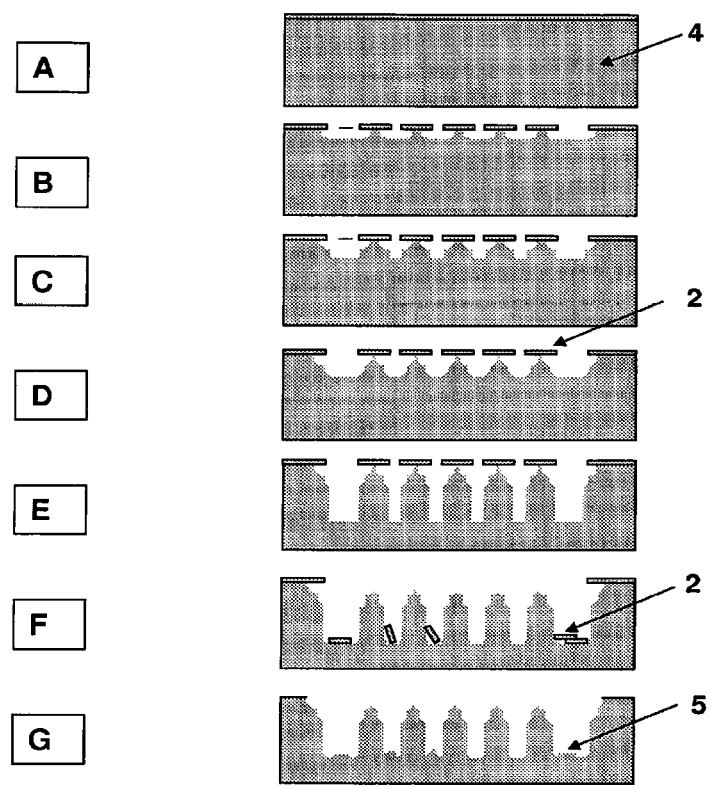
FIG. 1 shows a microneedle manufacturing process according to the state of the art.

1. Microneedle
2. Hat

3. Bridge
4. Wafer
5. Damaged area
6. Rectilinear segment
7. ½ circle
8. ¼ circle
9. Metal layer
10. SiO₂ layer State of the art MEMS microneedle fabrication process as described in FIG. 1 usually starts with a wafer, preferably a silicon wafer 4. On top of this silicon wafer a silicon dioxide layer is used as a protective mask to pattern the microneedles.

Figure 4:
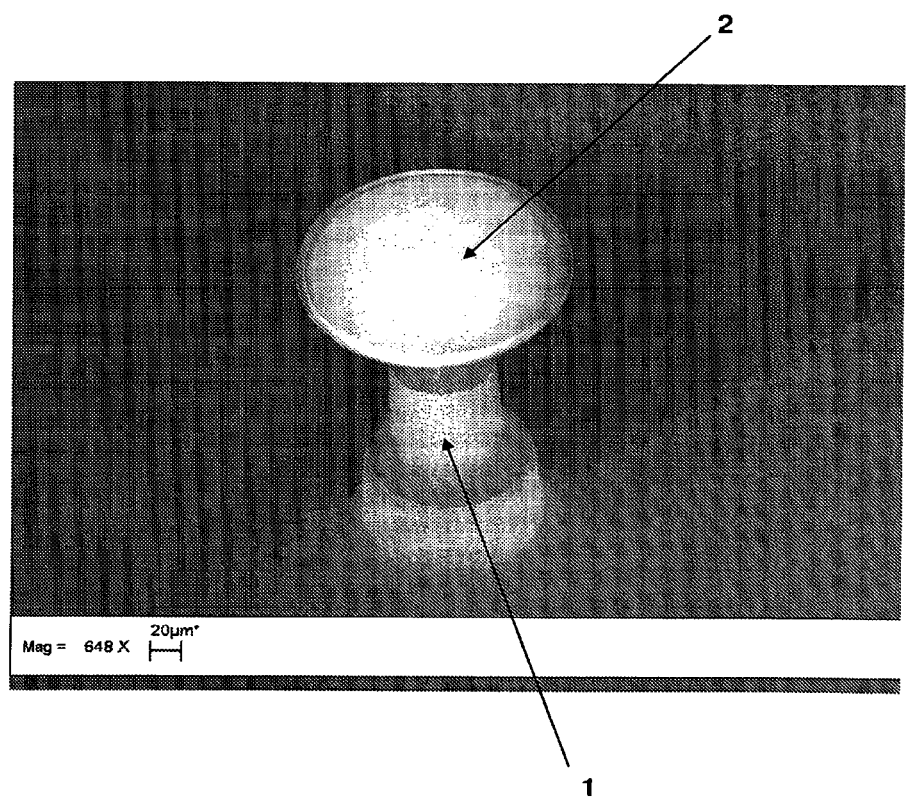
FIG. 4 is a picture of an assembly microneedle-hat according to the state of the art (without bridges)

This process aims at obtaining microneedles separated from each others and as a consequence the continuous protective mask in step A becomes discontinue at the start of the structuration of the microneedles step B. The parts of this discontinuous protective mask are called hats 2 and each microneedle is overlooked by a hat, protecting the microneedle and allowing controlled and well defined structuration. FIG. 4 shows an example of a microneedle creation 1 under a hat 2.

This structuration of the microneedles is performed by a sequence of isotropic and anisotropic etches as represented in FIG. 1 steps B to E.

The first isotropic etch as represented in FIG. 1 step B initiates the tip of the microneedle. The first anisotropic etch (FIG. 1, step C) is used to define the head of the microneedle.

The goal of the second isotropic etch as represented in FIG. 1 step D is to initiate the shoulder of the microneedle and to separate the head of the microneedle with the shaft which is obtain thanks to the second anisotropic etch (FIG. 1, step E).

Finally comes the last isotropic etch (FIG. 1, step F) which is the most important etch of the process. Thanks to this etch, we pattern the tip of the microneedle, the backside trough holes and the final design of the microneedle, An oxidation and a silicon oxide etch as represented in FIG. 1, step G are then realized to remove the hats and to polish the silicon surface.

Frequently hats may fall before the end of the process (FIG. 1, step F, Ref. 2): This leads to a situation in which the structuration of the microneedle becomes uncontrolled resulting in malformation and low production yields. In addition the fallen hats provoke a bad surface state as shown in FIG. 1 Ref 5.

Figure 2:
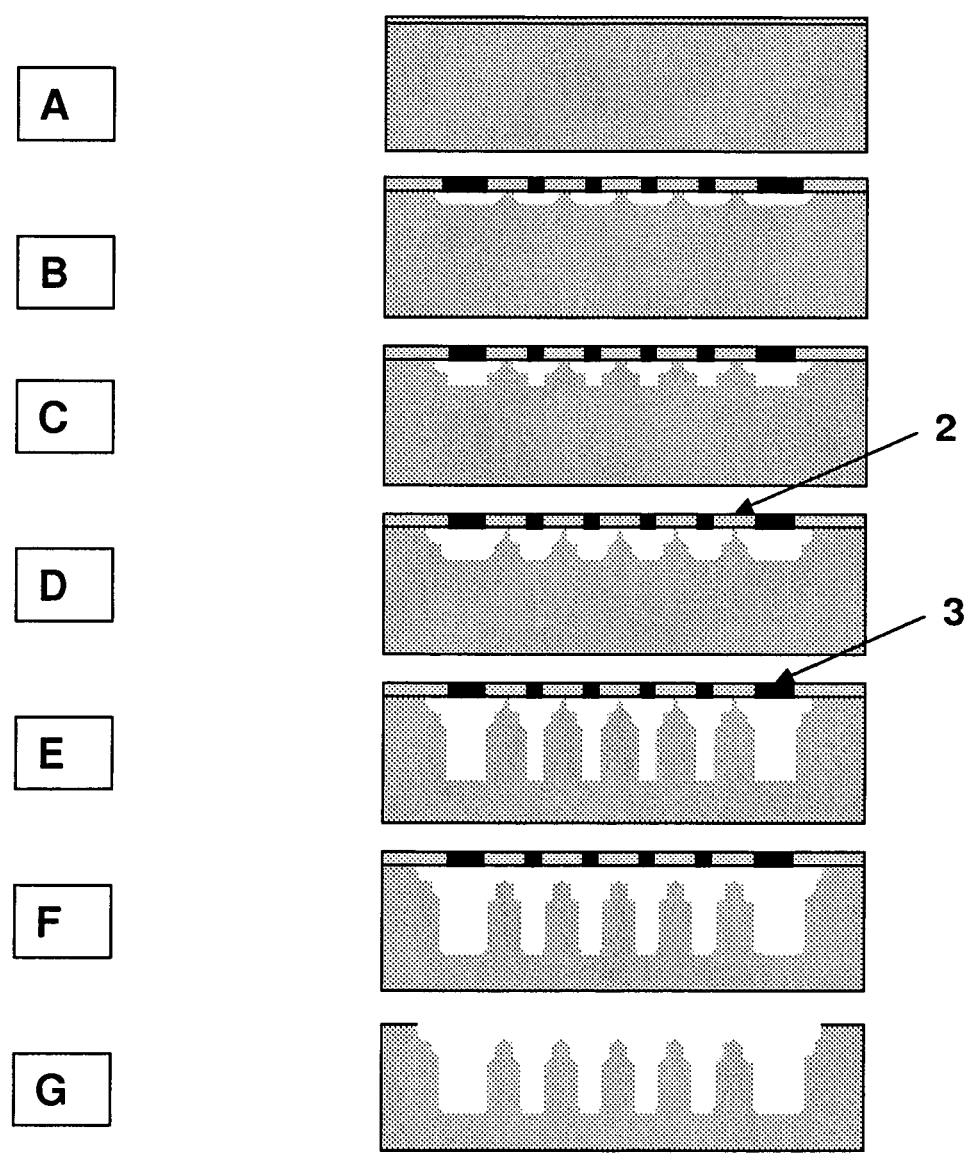
FIG. 2 (AA') shows a microneedle manufacturing process according to the invention.
Figure 3:
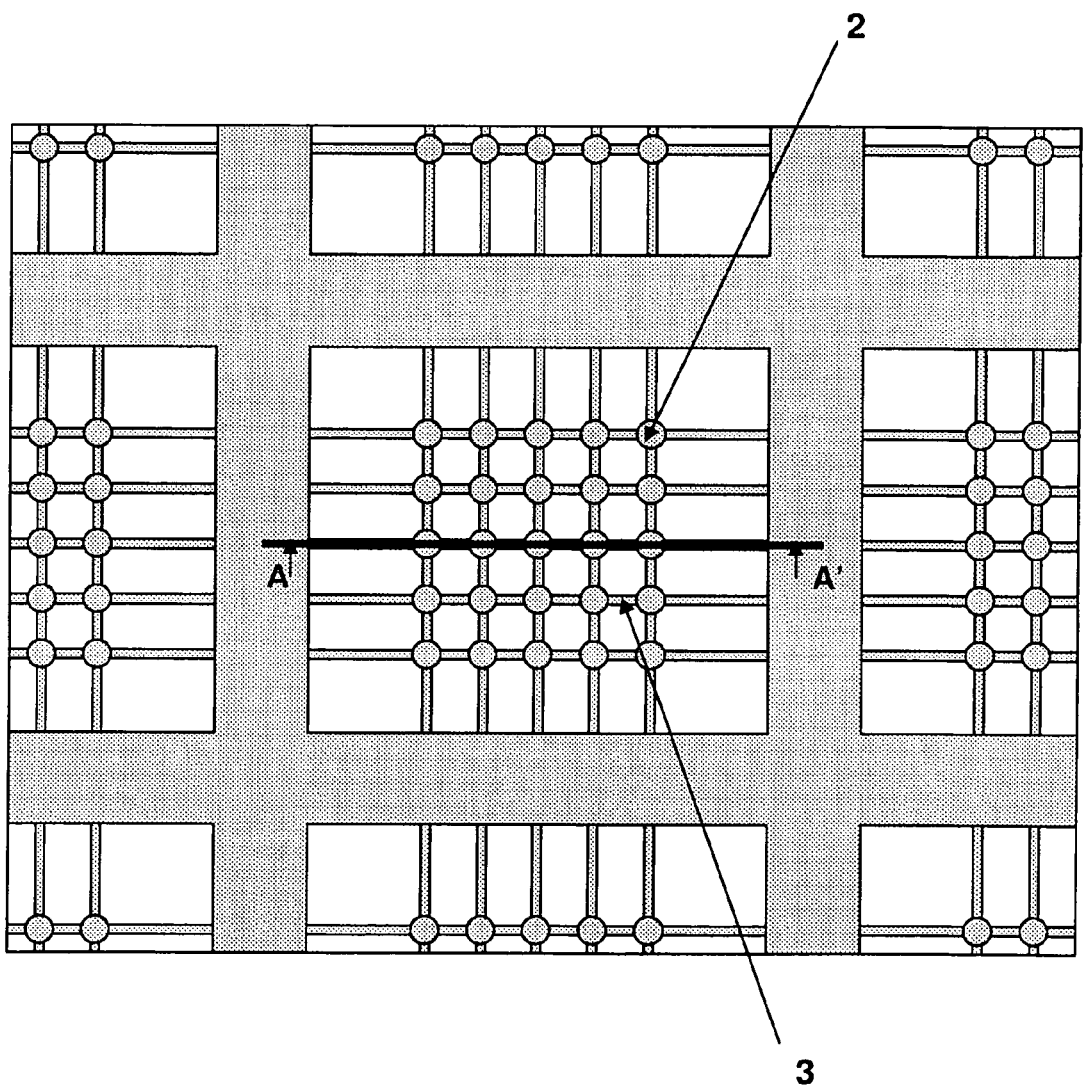
FIG. 3 is an upper view of the element shown in FIG. 2 (AA').
Figure 11:
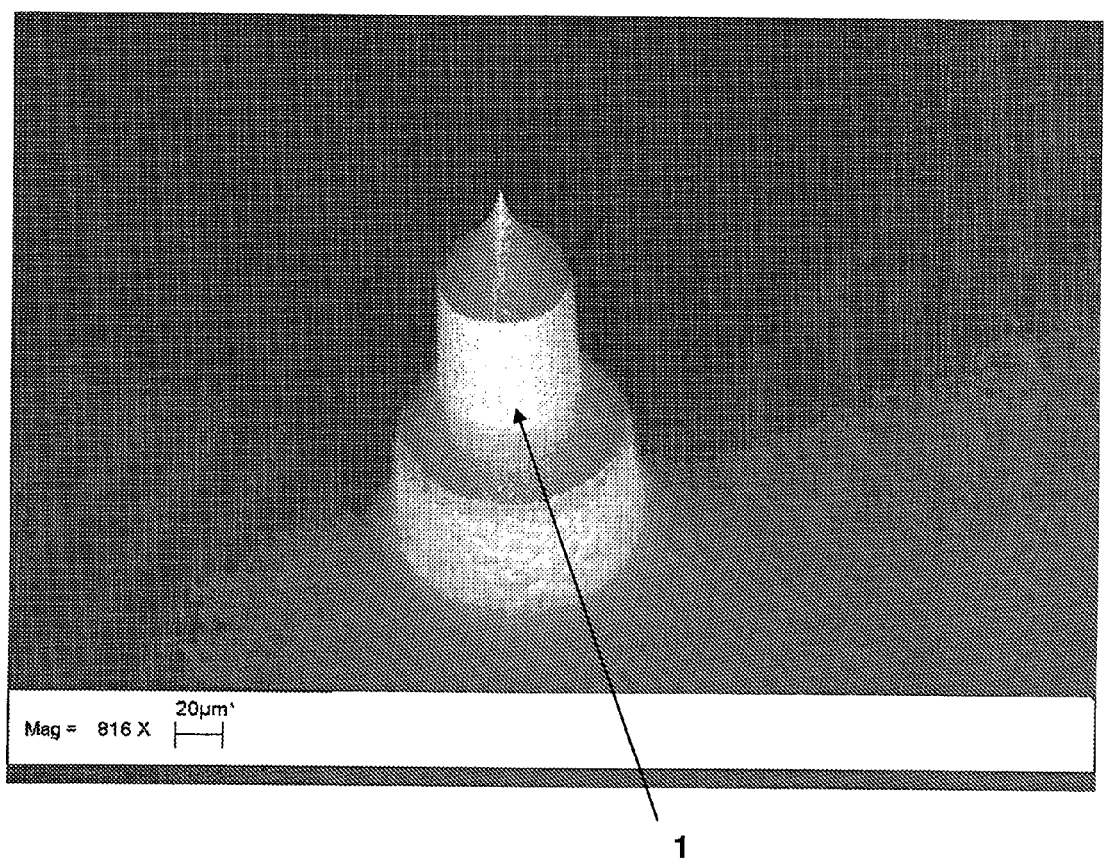
FIG. 11 is a picture of a microneedle obtained with a process according to the invention.

The present invention provides a way to hold the hats together so that they won't fall before the end of the process. To this effect the hats are linked together and are linked to the edges as displayed in FIG. 3. These links (FIG. 2, Ref 3), also named bridges in the present text, will stay in place up to the end of the process and guarantee the stability of each hat until the microneedle fabrication is ended (FIG. 2 Step F). When the process has been completed (FIG. 1 step G) the hat and their links are removed revealing perfect microneedles pattern (see e.g. FIG. 11) and chip surface state.

An important advantage of these links is that they do not modify the microneedle structuration parameters. The isotropic and anisotropic etches are the same with or without links.

As described earlier bridges and hats are deeply linked together; as a matter of fact their are made of same materials and have the same thickness.

Figure 5:
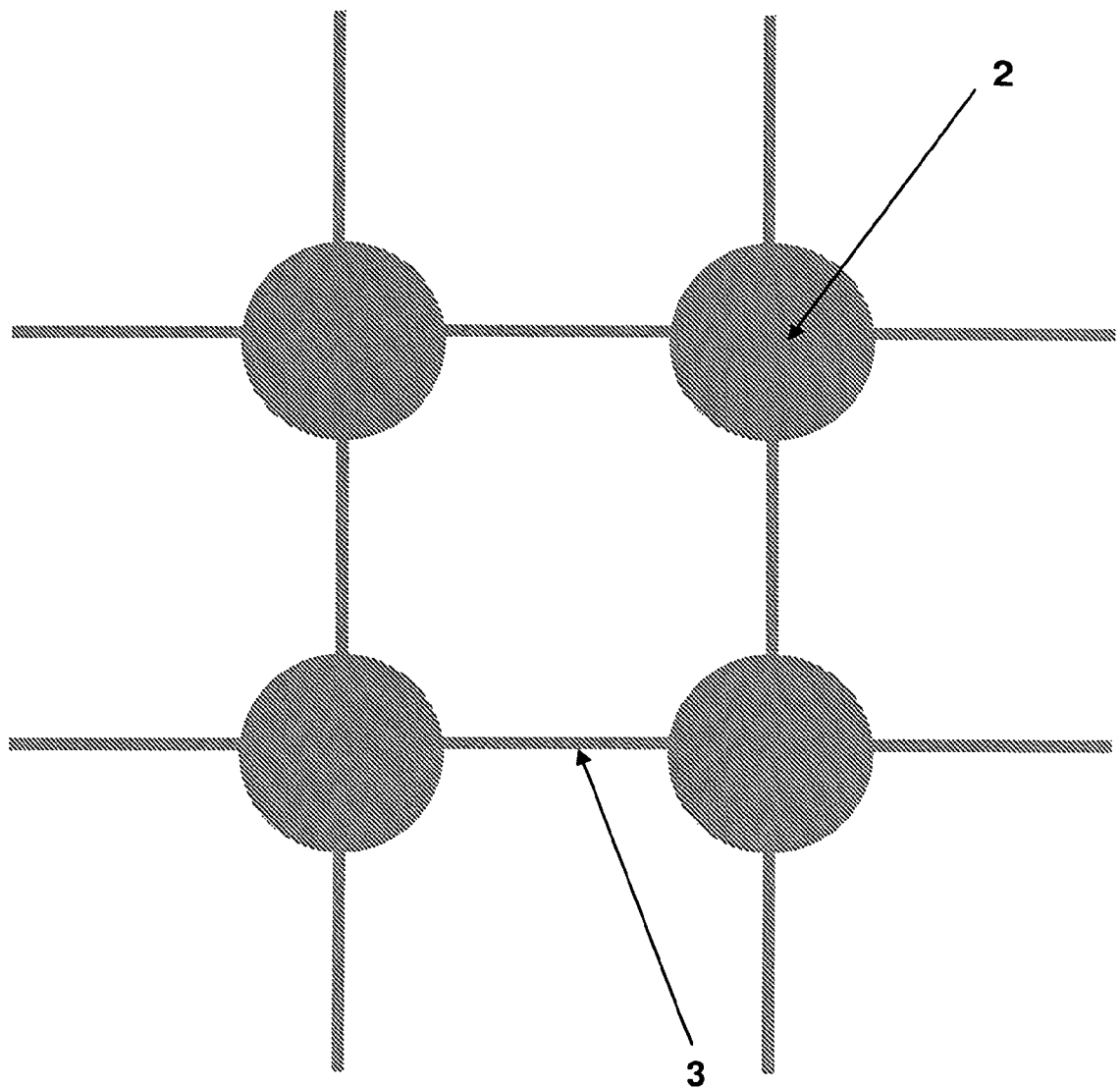
FIG. 5 shows one example of bridges according to the invention.
Figure 9:
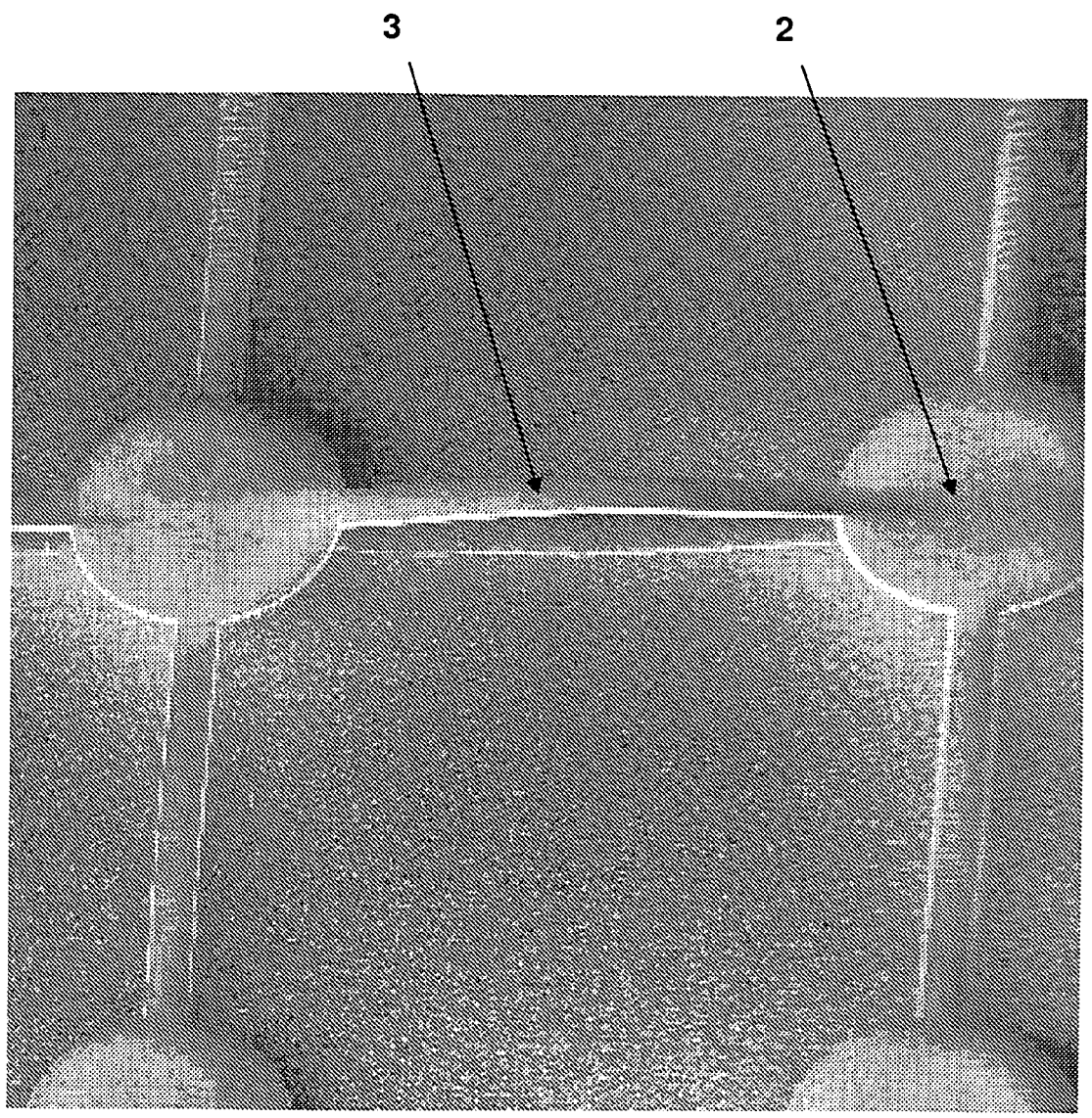
FIG. 9 is a picture of the example shown on FIG. 5.

As far as the design of the bridges is concerned it can take many forms. Simple linear bridge between the hats can be an option as shown schematically in FIG. 5 and on the picture in FIG. 9 which represents microneedle process of step B in FIG. 1.

Figure 6:
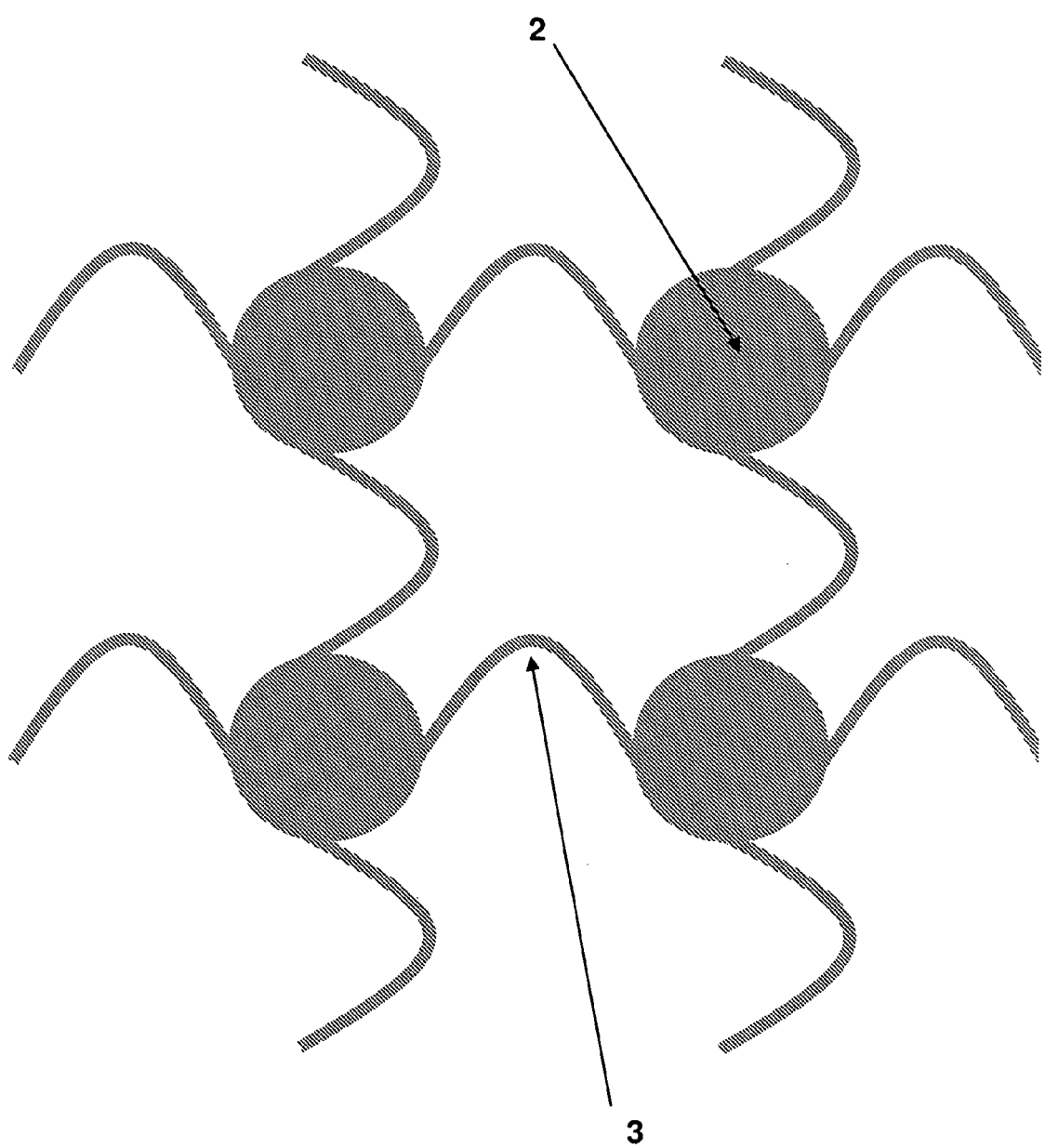
FIG. 6 shows another example of bridges according to the invention.
Figure 7:
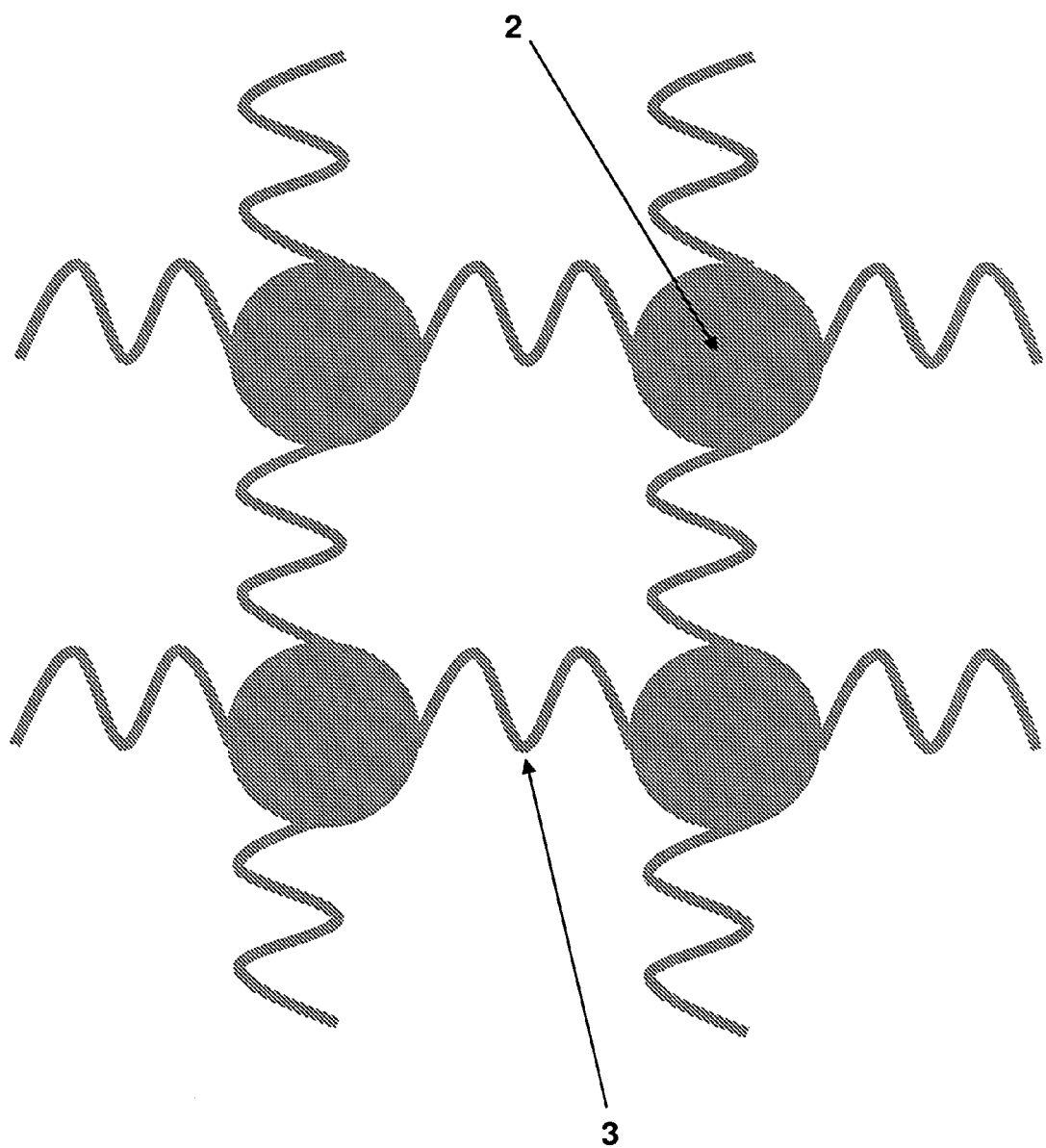
FIG. 7 shows another example of bridges according to the invention.
Figure 8:
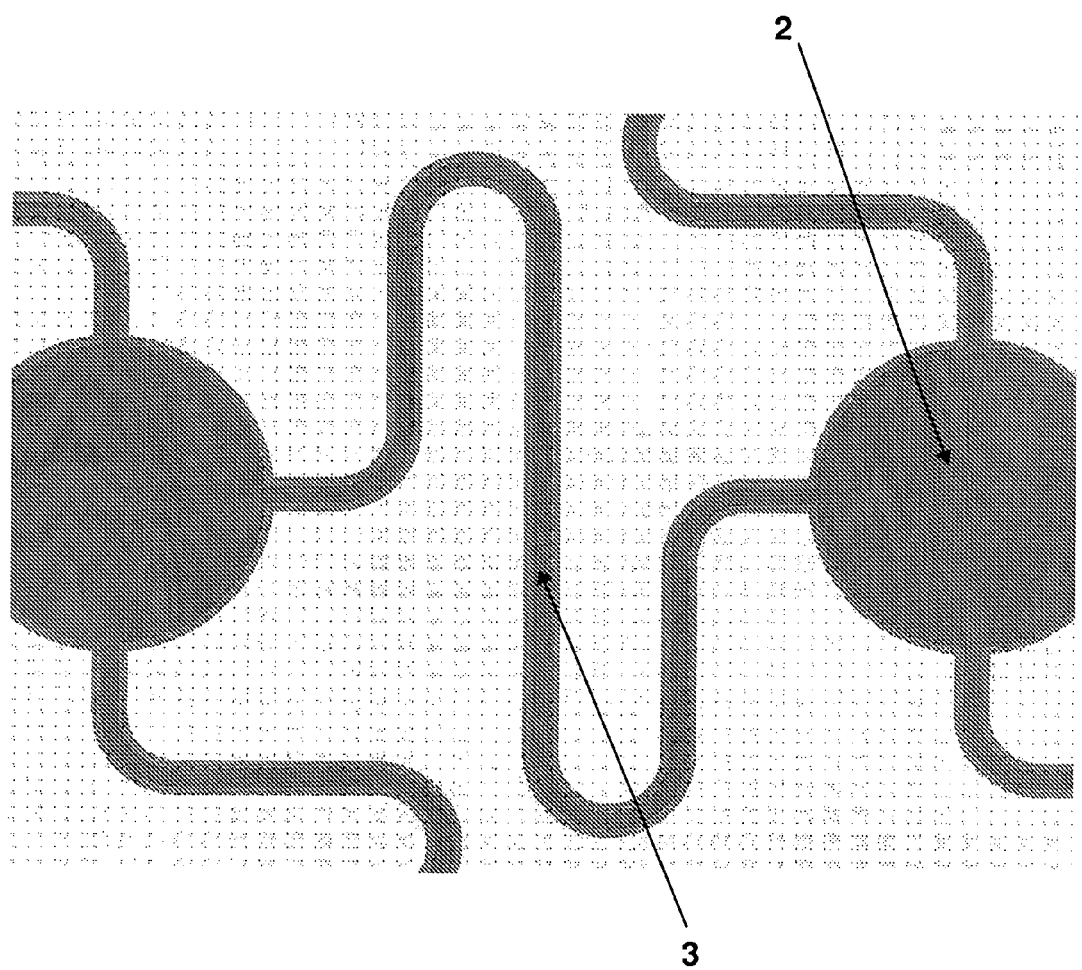
FIG. 8 shows another example of a bridges according to the invention.

Curved segments as in FIG. 6 and FIG. 7 or combination of rectilinear and curved segments as in FIG. 8 are also possible.

Figure 10:
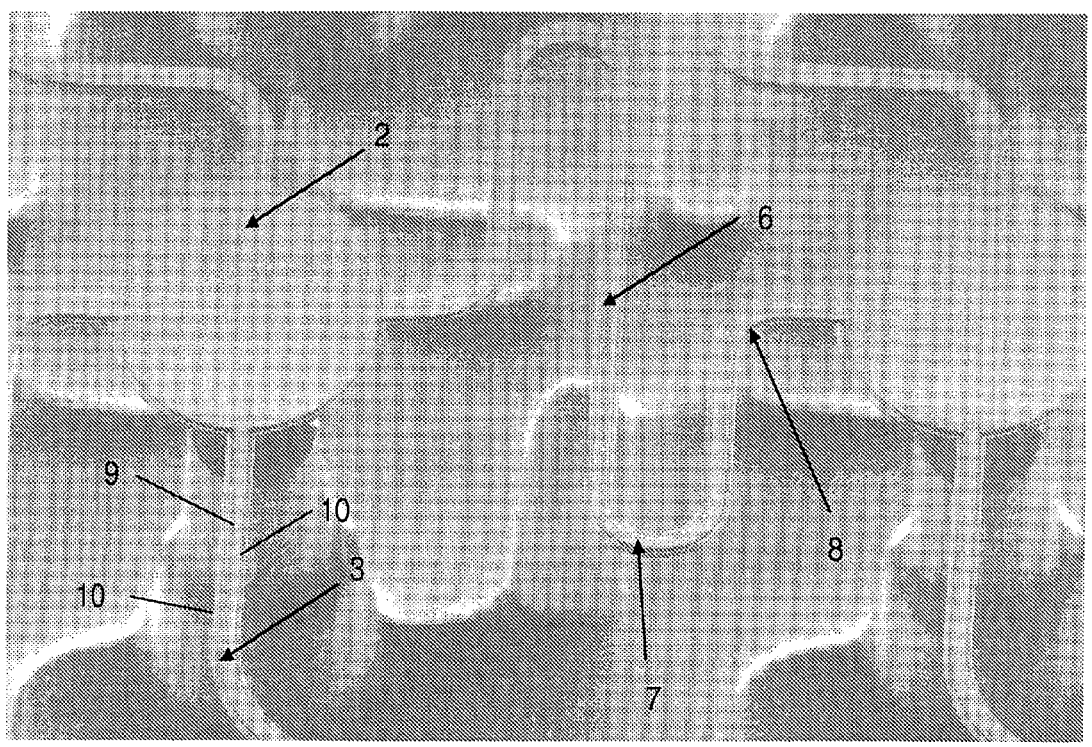
FIG. 10 is a picture of microneedles with hats and bridges before removal (status before FIG. 11)

Another aspect of the design of the bridges is the material. Single layer bridges can be appropriate for many processes but depending on the complexity of the process and also on the cleaning steps multilayer bridges can be a better option. Multilayered bridges improve the characteristics of the bridges (FIG. 10). We may associate metal layers (aluminium, tungsten, nickel . . . ) and no conductive layers (silicon dioxide, silicon nitride . . . ). The metal layers improve the thermal conductivity of the bridges and the non conductive layers improve the mechanical resistance and the high selectivity of the bridges.

The invention claimed is:

1. A suspended structure made of hats and bridges and obtained according to an out-of-plane microneedle manufacturing process comprising the simultaneous creation of a network of microneedles and the creation of a polygonal shaped hat above each microneedle under formation, said process further comprising the following steps:
   providing bridges between the hats,
   maintaining the bridges during the remaining microneedle manufacturing steps,
   wherein the bridges are at least partially curved and wherein the bridges and the hats are removed, when the microneedles are formed.

2. The suspended structure according to claim 1 wherein the bridges are multilayered.

3. The suspended structure according to claim 2 wherein the bridges are made of three layers, namely one conductive layer comprised between two non conductive layers.

4. The suspended structure according to claim 3 wherein the conductive layer is made of aluminum and the non conductive layers are made of silicon dioxide.

5. The suspended structure according to claim 1 wherein each bridge is made of a combination of rectilinear segments and of circle portions.

6. The suspended structure according to claim 5 wherein the circle portions comprise ½ circles and ¼ circles.

* * * * *